United States Patent
Bernardin et al.

(10) Patent No.: US 9,840,458 B2
(45) Date of Patent: Dec. 12, 2017

(54) THERMAL CONVERSION VESSEL USED IN A PROCESS FOR AMIDIFICATION OF ACETONE CYANOHYDRIN

(71) Applicant: Arkema France, Colombes (FR)

(72) Inventors: Yves Bernardin, Thionville (FR); Xavier Marcarian, Billere (FR); Romain Billon, Carrieres sur Seine (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/905,505

(22) PCT Filed: Jul. 18, 2014

(86) PCT No.: PCT/EP2014/065569
§ 371 (c)(1),
(2) Date: Jan. 15, 2016

(87) PCT Pub. No.: WO2015/007909
PCT Pub. Date: Jan. 22, 2015

(65) Prior Publication Data
US 2016/0137590 A1    May 19, 2016

(30) Foreign Application Priority Data
Jul. 19, 2013 (FR) .................................. 13 57134

(51) Int. Cl.
*C07C 231/12* (2006.01)
*C07C 57/04* (2006.01)
(Continued)

(52) U.S. Cl.
CPC ............. *C07C 231/12* (2013.01); *B01J 14/00* (2013.01); *B01J 19/002* (2013.01); *B01J 19/006* (2013.01);
(Continued)

(58) Field of Classification Search
None
See application file for complete search history.

(56) References Cited

U.S. PATENT DOCUMENTS 3,914,111 A * 10/1975 Anderson ................ B01J 14/00
                                                                422/200
4,269,805 A    5/1981 Schoengen et al.
(Continued)

FOREIGN PATENT DOCUMENTS

DE         2330716        8/1974
GB          808609        2/1959
(Continued)

*Primary Examiner* — Yate K Cutliff
(74) *Attorney, Agent, or Firm* — Thomas F. Roland

(57) ABSTRACT

The invention relates to a thermal conversion vessel (200) used during amidification step of acetone cyanohydrin (ACH), in the industrial process for production of a methyl methacrylate (MMA) or methacrylic acid (MAA). The thermal conversion vessel (200) is used for converting an hydrolysis mixture of α-hydroxyisobutyramide (HIBAM), α-sulfatoisobutyramide (SIBAM), 2-methacrylamide (MACRYDE) and methacrylique acid (MAA), into a mixture of 2-methacrylamide (MACRYDE). It comprises:—at least one compartment (C1, C2, C3, . . . C$i$) comprising an inner wall (206*a*, 206*b*, . . . 206*i*) separating said compartment into two communicating parts (C1*a*, C1*b*) by a passage provided between the bottom of said vessel and said inner wall,—said compartment having a space above said inner wall, for separating gas phase from liquid phase during thermal conversion,—said compartment being connected to an outlet valve (204*a*, 204*b*, . . . 204*i*). Such vessel allows obtaining a high yield thermal conversion in very safe conditions.

15 Claims, 3 Drawing Sheets

Figure 1:
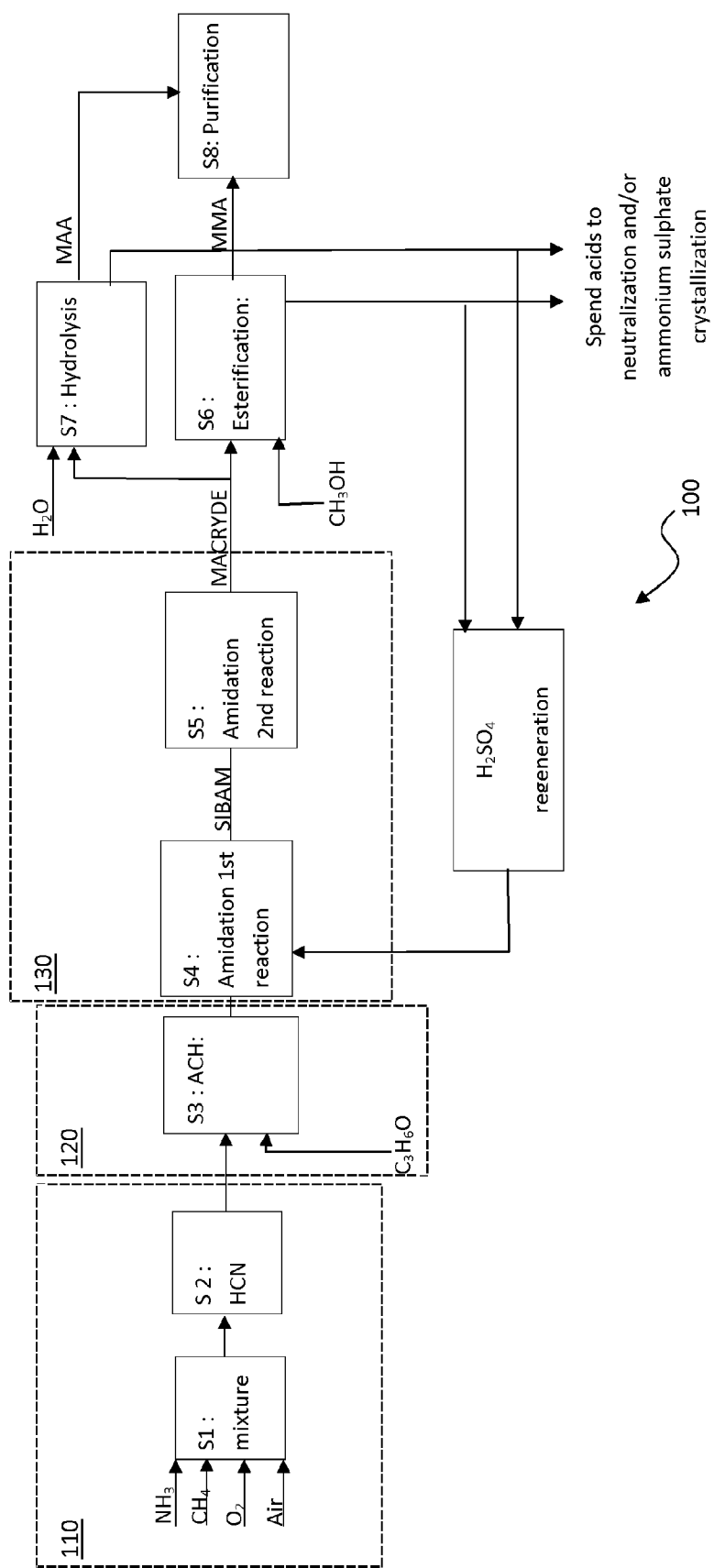

(51) Int. Cl.
*B01J 14/00* (2006.01)
*B01J 19/00* (2006.01)
*B01J 19/02* (2006.01)
*B01J 19/24* (2006.01)
*C07C 231/06* (2006.01)
*C07C 51/08* (2006.01)
*C07C 303/24* (2006.01)
*C07C 67/20* (2006.01)

(52) U.S. Cl.
CPC ........... *B01J 19/0013* (2013.01); *B01J 19/02* (2013.01); *B01J 19/245* (2013.01); *B01J 19/249* (2013.01); *C07C 51/08* (2013.01); *C07C 57/04* (2013.01); *C07C 67/20* (2013.01); *C07C 231/06* (2013.01); *C07C 303/24* (2013.01); *B01J 2219/0004* (2013.01); *B01J 2219/0027* (2013.01); *B01J 2219/00058* (2013.01); *B01J 2219/00063* (2013.01); *B01J 2219/00065* (2013.01); *B01J 2219/00162* (2013.01); *B01J 2219/00166* (2013.01); *B01J 2219/00182* (2013.01); *B01J 2219/00272* (2013.01); *B01J 2219/00768* (2013.01); *B01J 2219/029* (2013.01); *B01J 2219/0286* (2013.01); *B01J 2219/182* (2013.01); *B01J 2219/1943* (2013.01); *B01J 2219/2475* (2013.01)

(56) References Cited

U.S. PATENT DOCUMENTS

| | | | |
|---|---|---|---|
| 6,320,070 B1 * | 11/2001 | Aichinger | C07C 67/08 560/205 |
| 6,545,176 B1 * | 4/2003 | Tsay | B01J 19/02 560/179 |
| 2006/0111586 A1 | 5/2006 | Schladenhauffen et al. | |

FOREIGN PATENT DOCUMENTS

| | | |
|---|---|---|
| GB | 1435767 | 5/1976 |
| WO | WO2006/083251 | 8/2006 |
| WO | WO2007/081114 | 7/2007 |

* cited by examiner

THERMAL CONVERSION VESSEL USED IN A PROCESS FOR AMIDIFICATION OF ACETONE CYANOHYDRIN

This application claims benefit, under 35 U.S.C. §119 or §365 of PCT Application Number PCT/EP2014/065569 filed Jul. 18, 2014; and French Application Number FR 13.57134, filed Jul. 19, 2013.

FIELD OF THE INVENTION

The present invention relates to a continuous industrial process for the production of methyl methacrylate (MMA) or methacrylic acid (MAA). It relates more particularly to a step of such industrial process, which concerns the amidification step of acetone cyanohydrine. The invention relates more precisely to a thermal conversion vessel used during this amidification step for converting an hydrolysis mixture into a methacrylamide mixture, which is further either esterified to produce methyl methacrylate (MMA) or hydrolyzed in order to produce methacrylic acid (MAA).

STATE OF THE ART

A number of commercial processes are used to prepare monomer selected from methacrylic acid (also called "MAA" in the following description) and/or methyl methacrylate (also called "MMA" in the following description). One of these processes consists in preparing such monomer from acetone cyanohydrin (ACH). Such a process is for example described in US patent application US2010/0069662. In this process, acetone cyanohydrin ACH is hydrolysed by sulphuric acid to produce an hydrolysis mixture of α-hydroxyisobutyramide (also called "HIBAM" in the following description), its sulfate ester, α-sulfatoisobutyramide (also called "SIBAM" in the following description), 2-methacrylamide (also called "MAM" in the following description) and methacrylic acid MAA. The hydrolysis mixture thus produced is then thermally converted, into a heated thermal conversion reactor, to a mixture comprising 2-methacrylamide MAM and a small amount of MAA. During this reaction, the thermal conversion of SIBAM to MAM occurs more rapidly than the thermal conversion of HIBAM to MAM. In order to facilitate the thermal conversion of HIBAM to MAM, both heat and increased residence time of the mixture into the thermal conversion reactor must be provided. A decrease in thermal conversion to desired product (namely MAM) results in a decrease of overall yield for the process of production of MMA or MAA.

MAM can be used to produce MMA by reaction of esterification with methanol, or it can be used to produce MAA by reaction of hydrolysis with water.

Methyl methacrylate MMA is mostly used to produce polymer such as polymethylmethacrylate (also called "PMMA") which has multiple applications like for example automotive, transport, aerospace, photovoltaic, informatics, telecommunications, wind energy, or building construction. MMA can also be used to produce other methacrylates by mean of trans-esterification.

The MMA and MAA markets are extremely cost sensitive. A slight improvement in process yield can result in a significant market advantage.

Particularly, it has been discovered that, during the step of thermal conversion of SIBAM and HIBAM, a backmixing of the components of the hydrolysis mixture, namely HIBAM, SIBAM, MAM and MAA, appears into the thermal conversion reactor. Such a backmixing implies a variation of the retention time of each component of the mixture inside the thermal conversion reactor. Some of the components will have insufficient retention time inside the reactor, so that there is an low conversion of HIBAM. On the contrary, some of the components will have an extended retention time inside the thermal conversion reactor which can lead to a high conversion or degradation of SIBAM, MAM and MAA. Such a variation of the retention time inside the thermal conversion reactor degrades the thermal conversion step and thus, the overall yield of production of either MMA or MAA, is decreased.

For solving this problem of backmixing during the thermal conversion step, document EP 0999200 describes a thermal conversion reactor comprising a plug flow thermal conversion apparatus, which enables to avoid backmixing. Such plug flow thermal conversion apparatus is a pipe whose diameter is such that it allows having a velocity of the fluid in the pipe that is nearly the same throughout the cross section of the pipe. The velocity being the same all along the pipe, it prevents the apparition of a backmixing. In this document, the pipe has to have a sufficient length to provide the desired retention time of the mixture into the cracker reactor.

Nevertheless, such plug flow thermal conversion apparatus presents other inconvenient. Indeed, such apparatus requires, for the conversion reaction and for providing the desired retention time, several turns, long length of pipe, and several welding seams, latter which are sensitive to corrosion issues. Due to the fact that the length of the pipe has to be sufficient to have a desired retention time, and because the constitution material is a specific alloy such as Hastelloy® B, B2 or B3 (nickel/molybdenum alloy), such pipe is very expensive. Moreover, such pipe is difficult to clean and to maintain.

Furthermore, once the length has been chosen for a retention time, it is no more possible to change the length, so that the temperature of the mixture and the flow rate of the mixture feeding the pipe have to be very precise. For the adjustment of the flow rate, the pipe described in this document has a gradual expansion part at the input and a gradual constriction part at the outlet. However this pipe is not flexible and it is very difficult to have the optimal conditions, namely the temperature, the feeding flow rate and the desired retention time, because once the diameter and the length have been chosen, they can no more be changed easily. Thus, with such pipe, it appears impossible to adjust to the production of final monomer product, namely either MMA or MAA.

Finally, during the thermal conversion, the decomposition of the components leads to gas releasing. However, nothing seems intended in the pipe to remove the produced gases. Consequently, if the pressure of the gases increases and becomes too high inside the pipe, rupture of reactor may occur.

The document WO2006/083251 discloses a method for performing chemical reactions in a continuous segmented plug flow reactor. The plug flow reactor comprises heat transfer elements in each internal reaction chamber. Beside for promoting a high heat transfer, the heat transfer elements are also there for having a turbulent flow in each reaction chamber for more uniform mixing. Each chamber can also comprise additional mixing elements. The reactor contains only one outlet at the end. This is inconvenient so that the desired retention time of the reaction mixture with the desired product in the reactor can not be adapted in view of the productivity and conversion.

The document DE2330716 discloses apparatus for continuously carrying out chemical reactions in liquid phase. The apparatus comprises a stirring device in each compartment. The respective stirring devices are fixed to shaft crossing the whole apparatus. The stirring device perturbs the laminar flow in the apparatus.

Therefore, there is a need for improving the step of thermal conversion in order to increase the yield of thermal conversion, while maintaining safety.

Technical Problem

Present invention aims to avoid at least one of the inconvenient of the state of the art. More particularly, the invention aims to propose a simpler thermal conversion apparatus, which avoids backmixing of the components and enables to have a controlled retention time whatever the feed rate of the liquid mixture and the temperature inside the apparatus which is safe and avoids any risks of breakage due to overpressure.

BRIEF DESCRIPTION

For this purpose, the invention relates to a thermal conversion vessel for converting an hydrolysis mixture of α-hydroxyisobutyramide (HIBAM), α-sulfatoisobutyramide (SIBAM), 2-methacrylamide (MACRYDE) and methacrylic acid (MAA), into a mixture comprising 2-methacrylamide (MACRYDE), said vessel being characterized in that it comprises:
  at least one compartment comprising an inner wall separating said compartment into two communicating parts by a passage provided between the bottom of said vessel and said inner wall,
  said compartment having a space above said inner wall, for separating gas phase from liquid phase during thermal conversion,
  said compartment being connected to an outlet valve.

Thus, the thermal conversion vessel of the invention allows to separate two phases, namely the gases from the thermal decomposition of the mixture are separated from the liquid phase, which is located below the gas phase, so that it becomes possible to discharge the gases and to control the pressure inside the vessel for avoiding any risk of explosion. The inner walls allow avoiding a risk of backmixing because the mixture fills the compartment by flowing always in the same direction.

According to another particularity, the thermal conversion vessel comprises at least two compartments separated from each other by an overflow wall, over which the hydrolysis mixture to be converted flows to pass from one compartment to the other, each compartment being connected to an outlet valve.

Such a thermal conversion vessel, having more than one compartment, allows having a controlled and regulated residence time whatever is the feed rate of the liquid hydrolysis mixture. Indeed, if the feed rate is high, an outlet valve, distant from the feeding opening, is opened to create an output for the produced MAM. On the contrary if the feeding rate is low, then it is an outlet valve, which is close to the feeding opening, which is opened to create an output for the produced MAM. As for the inner walls, the overflow walls allow avoiding a risk of backmixing because they force the liquid to flow always in the same direction. The vessel of the invention is therefore flexible and it becomes possible with this vessel to adjust the temperature inside the vessel according to the residence time. The residence time is controllable whatever the feed rate of the mixture to be converted because, depending on the flowrate of the mixture filling the vessel, the outlet valve to be open will be more or less far from the feeding opening. Consequently, the residence time is maintained optimum to have a high yield of conversion, and the vessel allows a lot of flexibility because it adjusts the feed rate to the desired production without any consequences on the yield of thermal conversion.

According to another aspect, the invention relates to a unit for amidification of acetone cyanohydrin (ACH) into a mixture comprising 2-methacrylamide (MACRYDE), said unit comprising a first equipment for hydrolyzing acetone cyanohydrin (ACH) by sulphuric acid to produce an hydrolysis mixture of α-hydroxyisobutyramide (HIBAM), α-sulfatoisobutyramide (SIBAM), 2-methacrylamide (MACRYDE) and methacrylic acid (MAA), said unit being characterized in that it further comprises:
  heating means for heating said hydrolysis mixture at a temperature comprised between 110° C. and 165° C., preferably between 125° C. and 150° C. and more preferably between 130° C. and 145° C.,
  thermal conversion vessel described above, into which said heated hydrolysis mixture is introduced and flows through at least one compartment(s) during a predetermined retention time, during which said hydrolysis mixture converts into said mixture comprising 2-methacrylamide.

In order to avoid a decrease of yield this mixture comprising 2-methacrylamide is preferably not stored. Thus, the obtained mixture comprising 2-methacrylamide flows through at least one outlet valve of the vessel and is directed to next reaction step of the global process for the production of a monomer selected from methacrylic acid (MAA) and/or methyl methacrylate (MMA).

According to another aspect, the invention relates to a process for amidification of acetone cyanohydrine (ACH) comprising a first step of hydrolyzing acetone cyanohydrine by sulphuric acid to produce an hydrolysis mixture of α-hydroxyisobutyramide (HIBAM), α-sulfatoisobutyramide (SIBAM), 2-methacrylamide (MACRYDE) and methacrylic acid (MAA), and a second step of thermally converting said hydrolysis mixture into a mixture comprising 2-methacrylamide (MACRYDE), said process being characterized in that said second step of thermal conversion comprises following steps:
  heat said hydrolysis mixture to a predetermined temperature between 110° C. and 165° C., preferably between 125° C. and 150° C. and more preferably between 130° C. and 145° C.,
  feed the vessel described above with said heated hydrolysis mixture at a predetermined feed rate,
  leave said hydrolysis mixture flowing through compartments of said vessel for a predetermined retention time, comprised between 3 and 16 minutes, preferably between 5 and 12 minutes, to produce said mixture comprising 2-methacrylamide,
  open all the outlet valve(s) of the vessel downstream from an outlet valve, which is determined depending on said predetermined retention time, and said predetermined feed rate.

Finally, invention relates to a process for preparing a monomer selected from methacrylic acid (MAA) and/or methyl methacrylate (MMA) comprising the steps of:
  preparing hydrogen cyanide (HCN) by the Andrussow process,
  preparing acetone cyanohydrin (ACH) from hydrogen cyanide and acetone, hydrolyzing acetone cyanohydrin (ACH) to produce an hydrolysis mixture comprising α-hydroxyisobutyramide, α-sulfatoisobutyramide, 2-methacrylamide and methacrylic acid, thermally converting said hydrolysis mixture in a thermal conversion apparatus with the necessary retention time to produce a mixture comprising 2-methacrylamide, reacting the obtained mixture comprising 2-methacrylamide in at least one reactor with a material selected from methanol or water to produce a monomer selected from methyl methacrylate (MMA) or methacrylic acid (MAA), said process being characterized in that the step of thermal conversion is made according to process for amidification of acetone cyanohydrin described above by using the vessel described above, connected upstream to heating means.

INTRODUCTION OF THE FIGURES

Figure 2:
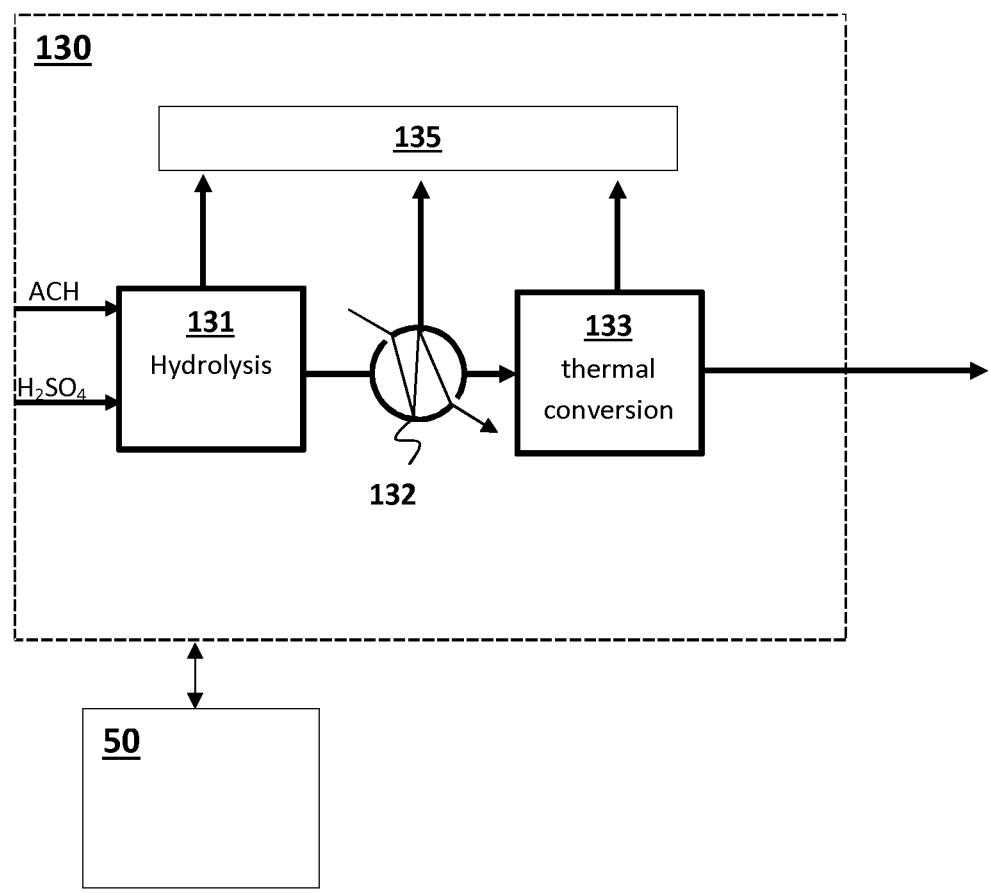
Figure 3:
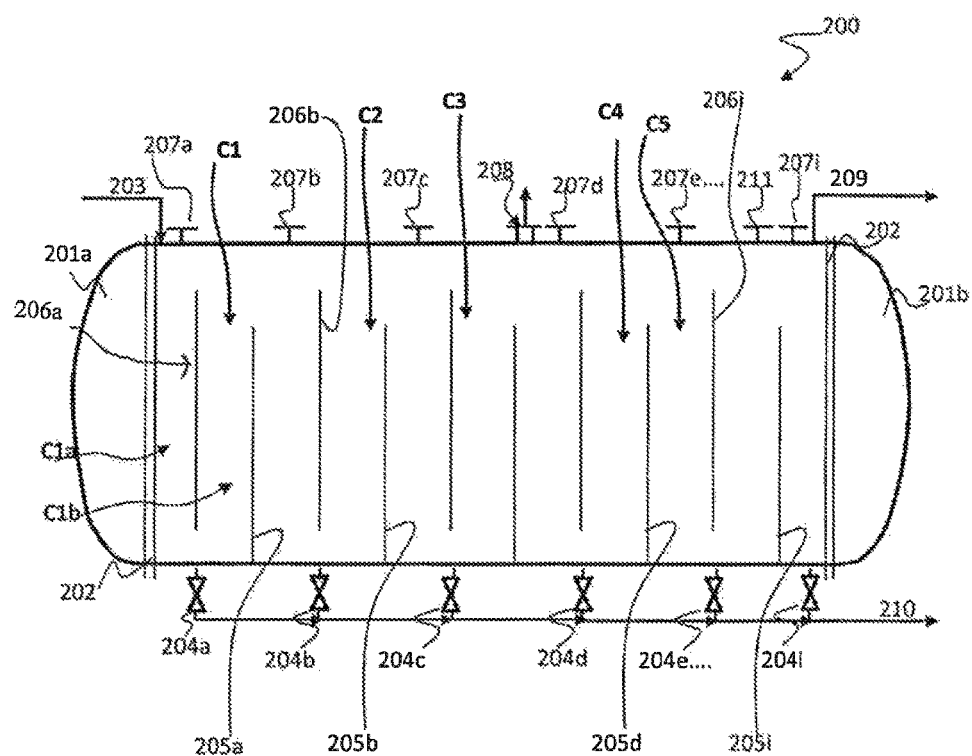
Figures 4A, 4B:
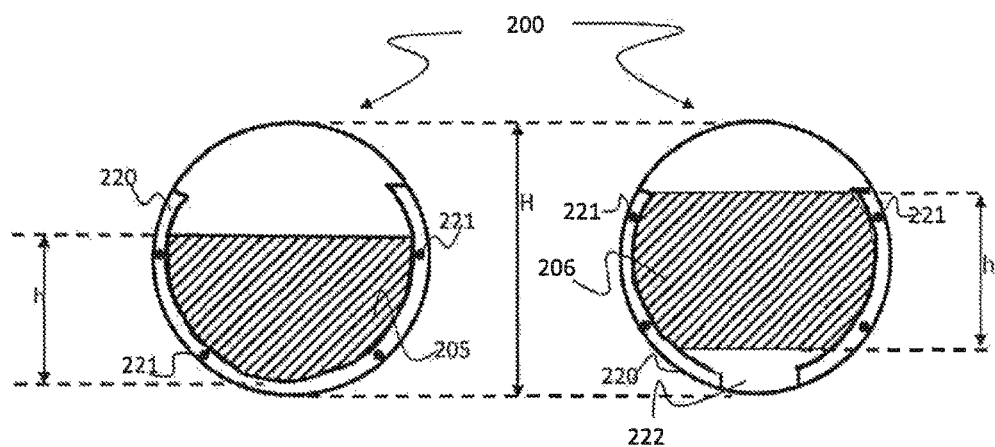

Other features and advantages of the invention will become apparent upon reading the following description given by way of illustrative and non-limiting examples, with reference to the accompanying Figures in which:

FIG. 1 represents a simplified schematic bloc diagram of a plant for preparing methacrylic acid and/or methyl methacylate, FIG. 2 represents a simplified schematic bloc diagram of a portion of plant of FIG. 1, corresponding to amidification section of the plant, FIG. 3 represents a schematic sectional view of a thermal conversion vessel of the invention, FIGS. 4A and 4B represent schematic sectional view along diameter of the vessel of FIG. 3, showing respectively an overflow wall and an inner wall.

SPECIFICATION

The thermal conversion vessel described in the specification has a substantially cylindrical shape, the height of the cylinder defining a horizontal axis of the vessel, parallel to the ground on which it is placed, and the diameter defining the vertical axis, perpendicular to the ground.

The terms "top", "upper" or "above" and "down", "bottom", or "below" are used to define a portion of the vessel with respect to the vertical axis of said vessel.

The terms "upstream" and "downstream" are defined relative to the direction of a fluid flowing through the devices of a plant for the production of a final product such as methylmethacrylate (MMA) or methacrylic acid (MAA).

Concerning the Synthesis of Monomer Selected from Methacrylic Acid and/or its Esters FIG. 1 shows a simplified schematic bloc diagram of a plant for the production of methacrylic acid and/or its esters from acetone and hydrogen cyanide HCN prepared by the Andrussow process. The Andrussow process is for example described in the document U.S. Pat. No. 1,934,838.

Such monomers can be further used to produce for example polymethylmethacrylate (PMMA) that is a polymer widely used in a lot of applications like for example automotive, transport, aerospace, photovoltaic, informatics, telecommunications, wind energy, or building construction . . . .

Preparation of Hydrogen Cyanide HCN

First of all (steps S1 and S2) HCN is produced in a first unit 110, from a mixture of methane-containing gas, ammonia and air eventually enriched with oxygen. A mixture of reactant gases is prepared (step S1), and introduced (step S2) into an Andrussow type reactor comprising catalyst gauzes based on platinum/rhodium gauzes. Mixture of gases passes over the catalyst gauzes and reacts at a temperature comprised between 750° C. and 1250° C. and preferably between 1000° C. and 1200° C., to form HCN. The oxygen-enriched air enables to increase the productivity and to reduce the methane consumption. The HCN produced is quickly cooled and treated so as to avoid polymerization of HCN. For that, ammonia which has not reacted is absorbed by reaction with sulfuric acid, and the HCN is absorbed and stabilized in an absorption column, and then distilled in a distillation column to reach a purity of 99.5% wt.

Preparation of Acetone Cyanohydrin ACH

The thus synthesized HCN is then mixed with acetone ($C_3H_6O$), in a unit 120 designed for the production of acetone cyanohydrin ACH (step S3). The crude acetone cyanohydrin obtained is then purified by distillation.

Amidification of Acetone Cyanohydrin

A third unit 130 of the plant is provided for amidification of acetone cyanohydrin. Such amidification of ACH requires two steps S4 and S5 for producing 2-methacrylamide (also called "MACRYDE" in the following description).

First, in step S4, sulphuric acid ($H_2SO_4$) is added in excess in comparison with acetone cyanohydrin ACH. For example the molar ratio of $H_2SO_4$/ACH is comprised between 1.25 and 1.8, more preferably between 1.3 and 1.6.

This first reaction occurring is an hydrolysis reaction of ACH by sulphuric acid, which gives an intermediate salt, called the SIBAM (for α-sulfatoisobutyramide). This reaction is the following:

$$(CH_3)_2COHCN + H_2SO_4 \rightarrow (CH_3)_2COSO_3HCONH_2 \qquad (1)$$

Acetone cyanohydrin (ACH) α-sulfatoisobutyramide (SIBAM)

This reaction is fast and exothermic. The temperature is around 90° C.-95° C. and the pressure is close to the atmospheric pressure.

The second reaction (step S5) is a slow and endothermic reaction. It occurs at atmospheric pressure and a temperature range between 110° C. and 165° C., preferably between 125° C. and 150° C. and more preferably between 130 and 145° C. This reaction is a cooking reaction which lasts between 3 and 16 minutes. This reaction is the following:

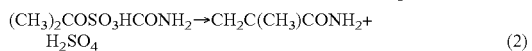

$$(CH_3)_2COSO_3HCONH_2 \rightarrow CH_2C(CH_3)CONH_2 + H_2SO_4 \qquad (2)$$

α-sulfatoisobutyramide (SIBAM) 2-methacrylamide (MACRYDE)

During the synthesis reactions there are many other by-products. The main side reaction is described below.

The first hydrolysis reaction of ACH by a small quantity of water can create a significant quantity of HIBAM (α-hydroxyisobutyramide). Such a reaction is very fast. It is the following:

$$(CH_3)_2COHCN + H_2O \rightarrow (CH_3)_2COHCONH_2 \qquad (3)$$

Acetone cyanohydrin (ACH) α-hydroxyisobutyramide (HIBAM)

In the second step S5, HIBAM can also create MACRYDE, but this reaction is very slow. So there is a large quantity of unconverted HIBAM at the end of amidification step S5. The reaction is the following:

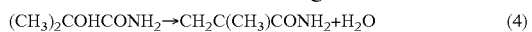

$$(CH_3)_2COHCONH_2 \rightarrow CH_2C(CH_3)CONH_2 + H_2O \qquad (4)$$

α-hydroxyisobutyramide (HIBAM) methacrylamide (MACRYDE)

The hydrolysis of HIBAM may create HIBA (α-hydroxyisobutyricacid):

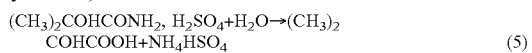

$$(CH_3)_2COHCONH_2, H_2SO_4 + H_2O \rightarrow (CH_3)_2COHCOOH + NH_4HSO_4 \qquad (5)$$

α-hydroxyisobutyramide (HIBAM) α-hydroxyisobutyricacid (HIBA)+ammoniumbisulfate

At the same time, a significant amount of methacrylic acid MAA is produced by the hydrolysis of SIBAM by water. This reaction is the following:

$$(CH_3)_2COSO_3HCONH_2+H_2O \rightarrow CH_2C(CH_3)COOH+ NH_4HSO_4 \quad (6)$$

α-sulfatoisobutyramide (SIBAM) methacrylic acid (MAA)+ammoniumbisulfate

The mixture of MACRYDE and MAA, also called mixture comprising 2-methacrylamide in the description, obtained after amidification is then either hydrolyzed (step S7), by adding water to the MACRYDE mixture, or esterified (step S6), by adding methanol to the MACRYDE mixture.

Esterification

The components obtained after amidification, namely the methacrylamide and the methacrylic acid, are esterified, so as to obtain methylmethacrylate MMA. The esterification reaction (step S6) is made by mixing said components with methanol ($CH_3OH$).

The main reactions are these two below:

$$CH_2C(CH_3)CONH_2, H_2SO_4+CH_3OH \rightarrow CH_2C(CH_3)COOCH_3+NH_4HSO_4 \quad (7)$$

methacrylamide (MACRYDE)+methanol methylmethacrylate (MMA)+ammoniumbisulfate $$CH_2C(CH_3)COOH+CH_3OH \rightarrow CH_2C(CH_3)COOCH_3+H_2O \quad (8)$$

methacrylic acid (MAA)+methanol methymethacrylate (MMA)

Hydrolysis

The components obtained after amidification can also be hydrolysed by mixing them with water (step S7). Such hydrolysis reaction allows to obtain methacrylic acid according to the following reaction:

$$CH_2C(CH_3)CONH_2, H_2SO_4+H_2O \rightarrow CH_2C(CH_3)COOH+NH_4HSO_4 \quad (9)$$

methacrylamide (MACRYDE) methacrylic acid (MAA)+ammoniumbisulfate

Purification of Crude MMA or MAA Obtained

Either the crude methylmethacrylate MMA obtained after esterification (S6) or the crude methacrylic acid MAA obtained after hydrolyse (S7) is then purified (step S8) by classical process known in the art, in order to remove residual compounds.

Concerning the Thermal Conversion Step by Means of a Thermal Conversion Vessel

FIG. 2 shows a simplified schematic bloc diagram of a portion of plant of FIG. 1, corresponding to amidification unit 130 of the plant. This unit 130 comprises first equipment 131 for hydrolyzing acetone cyanohydrin ACH by sulphuric acid $H_2SO_4$, to produce the hydrolysis mixture of α-hydroxyisobutyramide (HIBAM), α-sulfatoisobutyramide (SIBAM), 2-methacrylamide (MACRYDE) and methacrylic acid (MAA) (step S4 of the process for production of MMA or MAA). The thus synthesized hydrolysis mixture is then thermally converted into a mixture comprising 2-methacrylamide (MACRYDE) and a small amount of methacrylic acid (MAA). For that, the amidification unit 130 comprises heating means 132 for heating the hydrolysis mixture at a temperature which has to be comprised between 110° C. and 165° C., preferably between 125° C. and 150° C. and more preferably between 130° C. and 145° C., in order to ensure an optimal conversion of the hydrolysis mixture. Such heating is provided by means of a heat exchanger 132, functioning with a heating stream. The heated hydrolysis mixture is introduced into a thermal conversion vessel 133 for a predetermined retention time. The vessel is a confined vessel inside which the mixture is maintained at the conversion temperature during the predetermined retention time to have an optimal yield of conversion. When the retention time is reached, the mixture comprising 2-methacrylamide flows through at least one outlet valve of the vessel. The role of the outlet valves is to remove the desired product or mixture comprising the product from the reaction vessel after desired retention time. The role of the outlet valves in the present invention is not to remove by-products during the reaction.

Then the obtained mixture comprising 2-methacrylamide is quickly directed to next reaction step (step S6 or S7 in FIG. 1) of the process for preparing a monomer selected from methacrylic acid and/or methyl methacrylate, in order to avoid its polymerization.

Optionally, it is possible to provide cooling means immediately downstream the vessel.

Each of the equipment of this amidification unit 130, namely the hydrolysis equipment 131, the heating means 132, and the vessel 133 is equipped with at least one vent connected to a vent collection network 135, in order to discharge the gases that form due to the decomposition of the components of the mixtures in course of the amidification process.

The unit 130 could moreover be connected to a control unit 50 which manages several regulations alarms and safety interlocks, like for example, the temperature of the hydrolysis reaction 131, the feed flow rate of ACH and sulfuric acid, the heating temperature of said liquid hydrolysis mixture, and the cooling temperature of said mixture of methacrylamide at the output of the vessel. In other hand, the opening and/or closure of at least one outlet valve of said vessel 133 is controlled manually. Such a regulation allows having an optimal yield of conversion of the hydrolysis mixture into the mixture of methacrylamide in safe conditions. Spent acid ($H_2SO_4$) from esterification or hydrolysis maybe used to produce ammonium sulfate or maybe regenerated to produce sulfuric acid/oleum which can be recycled into the process.

FIG. 3 shows a schematic sectional view of the thermal conversion vessel. On this Figure, thermal conversion vessel is referenced 200.

This vessel has a substantially cylindrical shape, whose height defines a horizontal axis parallel to the ground on which it is placed. Thus, the vertical axis, perpendicular to the ground, is defined by the diameter of the cylinder.

This vessel comprises at least one compartment C1. On the FIG. 3 the vessel is schematized with six compartments. Preferably the vessel comprises at least two compartments and more preferably at least three compartments (C1, C2, C3, . . . Ci) comprising an inner wall (206a, 206b, . . . 206i) separating said compartment into two communicating parts (C1a, C1b) by a passage provided between bottom of said vessel and said inner wall. Preferably, the vessel comprises between 1 and 16 compartments, and more preferably between 2 and 12, advantageously between 3 and 12.

Each compartment has an inner wall 206a, 206b, . . . 206i, separating said compartment C1 into two communicating parts C1a and C1b, by a passage below said inner wall, for forcing the liquid mixture falling into first part C1a of said compartment to flow between the bottom of said compartment C1 and said inner wall 206a, and to get into the second part C1b of said compartment C1. The inner wall 206a, 206b, . . . 206i is fixed to the inner side wall of the vessel as in FIG. 4b. The inner wall is not rotatable or part of an agitating system.

A space is provided above said inner wall 206a, into the upper part of the vessel, located between top of the vessel and top of said inner wall 206a. Such space is provided for separating gas phase from liquid phase during the thermal conversion. Indeed, during thermal conversion of the hydrolysis mixture, there is a release of gas due to decomposition of methacrylamide in acetone, CO, HCN or $SO_2$. Such gas phase is separated from liquid phase and can be removed thanks to the presence of a vent outlet 209 which is connected to a vent network. Such gas outlet allows the vessel to operate below a pressure of 0.5 barg (i.e 0.5 bar above atmospheric pressure). Thus, risks of explosion are highly decreased with such separation of phases and gas outlet.

Preferably, the vessel comprises more than one compartment. More preferably the vessel comprises at least three compartments. For that, each compartment C1, C2 . . . Ci is separated from each other by an overflow wall 205a, 205b . . . 205i. The term "overflow wall" means a wall above which a liquid mixture flows to pass from one compartment to another. Such overflow walls are provided so that the liquid mixture feeding the vessel flows from one compartment to the next by flowing over each overflow wall. Thus, the hydrolysis mixture flows into the first compartment C1, in such a manner that it falls into first part C1a of said first compartment, flows between the bottom of said compartment C1 and said inner wall 206a, and gets into the second part C1b of said compartment, then it continues flowing over overflow wall 205a for falling into the first part C2a of the second compartment C2 etc . . . .

Each compartment is advantageously connected to an outlet valve 204a, 204b, 204c, . . . 204i. The opening 203 of the vessel 200, through which the hydrolysis mixture is fed, is disposed at the top of the vessel, above the first compartment. Each outlet valve of each compartment is disposed at the bottom of the vessel, just below each compartment, and connected to an exit 210. The task of the outlet valves is to remove a mixture comprising the desired product from the reaction vessel after the desired retention time. The outlet valves in the present invention are not there to remove by-products only during the reaction.

The inner walls and overflow walls are of the same height but are not disposed identically inside said vessel. Indeed, the inner walls are disposed so as to provide a communicating passage at the bottom, between two parts of a compartment, while the overflow walls are disposed to separate each compartment so that they don't provide any communicating passage at the bottom between each compartment.

All overflow walls and inner walls allow to avoid apparition of stagnate area and backmixing of the liquid mixture. The liquid mixture falls from the opening 203 located at the top of the vessel, and its flow is always guided so as to fill successively a first part of a compartment and the second part, and then pass over an overflow wall to continue to fill an adjacent compartment in the same manner. Backmixing being avoided, a large decomposition rate of mixture comprising 2-methacrylamide (MACRYDE) is thus avoided.

The overall number of overflow walls and inner walls is advantageously comprised between 3 and 32, and preferably between 5 and 28 and more preferably between 10 and 24.

A laminar flow is obtained and according to the invention a turbulent flow should be avoided. The vessel according to the invention comprises no agitator or mixing element. By agitator or mixing elements are meant devices or elements that disturb the laminar flow in order to create turbulences. This can be a classic agitator with a rotatable axis and stirring elements or baffles or introduction of gas bubbles. None of the latter elements is present in the vessel according to the invention.

FIGS. 4A and 4B represent schematic sectional view along diameter of the vessel of FIG. 3, showing respectively an overflow wall 205 and an inner wall 206.

Side walls of the vessel 200 comprise flanges 220 regularly spaced. Such flanges are provided for fixing said overflow 205 and inner 206 walls. For that, each overflow and inner wall is fixed at some points 221 of each flange 220, by means of screw and nut or rivet, or other equivalent means. The overflow wall 205, schematized on FIG. 4A, is fixed in such a manner that there is no communicating passage into the lower part of the vessel. On the contrary, the inner wall 206, schematized on FIG. 4B, is fixed in such a manner that its position is shifted to upper part of the vessel, relative to overflow wall, so that a communicating passage is provided in the lower part of the vessel. On this Figure, one can see that the flange 220 has also an opening 222 provided at the bottom, so that the liquid mixture can flow through the communicating passage without any obstacle which could hinder the flow.

The height h of the overflow walls 205 and the inner walls 206 is identical. This height is determined so as to preserve a sufficient space in the vessel, above the walls, for the gas phase. Therefore, the height h of either overflow walls or inner walls is preferably comprised between $\frac{2}{3}$ and $\frac{3}{4}$ of the height H of the vessel 200.

Such a vessel is thus flexible because it allows adapting to the desired productivity. If the quantity of final product to produce is increased, then the flow rate of the hydrolysis mixture feeding the vessel is increased. Despite this increase of feed rate, the retention time inside the vessel is maintained constant so as to have an optimal conversion of the hydrolysis mixture in the mixture comprising MACRYDE. Indeed, when the feed rate is increased, then the liquid flows quicker in the compartments of the vessel, over the overflow walls, and fills more compartments during the same time than with a lower feed rate. Consequently, in order to have always the same retention time, the outlet valves which are open to exit the obtained mixture comprising MACRYDE will be farther from the feeding opening 203 of the vessel. For example, with an increased feed rate, the outlet valves disposed downstream from outlet valve 204e will be opened, while all the outlet valves disposed upstream the outlet valve 204e remain closed.

On the contrary, if the desired productivity decreases, then the feed rate of hydrolysis mixture is decreased, so that the liquid mixture flowing through the compartments fills fewer compartments during the same time than with a quicker feed rate. Consequently, in order to have the same constant retention time inside the vessel, so as to have an optimal conversion reaction, the outlet valves which are open to exit the obtained mixture comprising MACRYDE will be closer from the feeding opening 203 of the vessel. For example, with a decreased feed rate, the outlet valves disposed downstream from outlet valve 204b will be opened.

Moreover, the temperature is advantageously adjusted depending on the desired retention time. Indeed, optimum of the conversion reaction depends on temperature and retention time. Retention time is advantageously comprised between 3 and 16 minutes, and preferably between 5 and 12 minutes. Thus, according to the selected retention time, the temperature of the mixture, which is heated before its introduction into the vessel, is adjusted, inside the optimum range of 110° C. to 165° C., preferably between 125° C. and 150° C. and more preferably between 130° C. and 145° C., to have the best rate for the conversion.

The vessel being a confined space, the temperature of the mixture is maintained substantially constant. In fact a slight increase or conversely slight decrease of temperature can be observed due to two competitive phenomena. The first phenomenon concerns the partial decomposition of methacrylamide which is exothermic. The second phenomenon is due to the natural external environment of the vessel which slightly cools the mixture across the vessel's walls. Anyway, such variation of temperature inside the vessel never exceeds 5° C.

In case of bad temperature regulation, the reaction might become a runaway reaction. Therefore, it might generate a huge quantity of gas and entail an overpressure. In order to avoid such a situation, a bursting disk 208 is advantageously provided on top of the vessel. Such a bursting disk thus prevents any risks of explosion and makes the vessel safe.

The vessel comprises also, at least at one end, but preferably at each end, a manhole 201a, 201b.Thus, each manhole can be opened for example by pivoting around a rotation axis that is fixed on a flange 202 for example. Such a configuration of the vessel is advantageous because it facilitates the cleaning of the vessel. Indeed, it appears necessary to clean regularly the vessel, for example once per year, in order to remove polymers which can fall at the bottom of the vessel.

Preferably, an inhibitor is mixed into sulfuric acid that is used in the first reaction of amidification that leads to the liquid hydrolysis mixture, which is then fed into the vessel before amidification reaction. The inhibitor allows to prevent the polymerization of the 2-methacrylamide (MACRYDE) obtained in the mixture after the thermal conversion. Such inhibitor has to be soluble in sulfuric acid such as phenothiazine.

In order to resist to the corrosive mixture, the vessel and its overflow and inner walls is preferably made of alloys chosen at least amongst: nickel based alloys and preferably nickel/molybdenum alloys as Hastelloy® B, B2, B3; iron/nickel alloy as Incoloy® or Tantalum alloys.

Finally, vessel is provided with several sensors at the top. On FIG. 3, is represented one temperature sensor 207a, 207b . . . 207i, per compartment, placed above each compartment. However the number of temperature sensors may be more or less. In fact, there are at least two temperature sensors placed respectively at each end of the vessel, in order to control that the temperature is constant all along the vessel. There is also at least one pressure sensor 211 in order to control the quantity of gas formation above the liquid phase.

The vessel 200 allowing thermal conversion of hydrolysis mixture previously obtained in a first equipment of the amidification unit 130 of a plant for producing either MMA or MAA that has been described, brings a lot of benefits. More particularly, such vessel allows to obtain a high yield thermal conversion in very safe conditions, because liquid and gas phases are separated and gas is discharged through vent, so that pressure is maintained constant inside the vessel, slightly more than atmospheric pressure.

Such separation of liquid and gas phase is impossible with a plug flow pipe described in the previously cited document EP 0 999 200. In order to avoid the formation of gas bubbles in the liquid flowing through this plug flow pipe, it is necessary to maintain a pressure that has to be much more than the atmospheric pressure, which can become problematic in terms of safety, because in case of runaway of the conversion reaction, it may be not possible to avoid an explosion.

Moreover, for having the same retention time of the mixture inside the vessel, the vessel of the present invention needs less surface of alloy than the pipe of prior art. Thus, the vessel of the present invention is therefore less expensive than the pipe of prior art.

Furthermore, the pipe of prior art has a fixed length and is therefore configured for only one feed rate, in order to have the optimum retention time. Such pipe is therefore configured for a fixed quantity of production. On the contrary, vessel of the present invention is flexible. Indeed, this last one allows to have a constant retention time of the mixture whatever is the feed rate, and therefore whatever is the desired productivity. Consequently, the vessel of the invention can adapt to changes in production.

While the plug flow pipe of the prior art requires a lot of turns, and therefore a lot of welding seams going through the tube from the inside to the outside, for having the desired retention time, the vessel of the present invention does not need so many weld seams so that it is less sensitive to corrosion and consequently more resistant.

Finally, while the plug flow pipe of the prior art cannot be easily cleaned, the vessel of the present invention can be easily and regularly cleaned.

The invention claimed is:

1. Process for amidification of acetone cyanohydrine (ACH) comprising a first step of hydrolyzing acetone cyanohydrine by sulphuric acid to produce an hydrolysis mixture of α-hydroxyisobutyramide (HIBAM), α-sulfatoisobutyramide (SIBAM), 2-methacrylamide (MACRYDE) and methacrylic acid (MAA), and a second step of thermally converting said hydrolysis mixture into a mixture comprising 2-methacrylamide (MACRYDE), wherein said second step of thermal conversion comprises the following steps:
heating said hydrolysis mixture to a predetermined temperature between 110 and 165° C.,
feeding a thermal conversion vessel (200) having a top and a bottom and having side walls, with said heated hydrolysis mixture at a predetermined feed rate, wherein said vessel (200) comprises at least three compartments (C1, C2, C3, . . . Ci) separating said compartments into at least three communicating parts (C1a, C1b, . . . C1c, by a passage provided between the bottom of said vessel and an inner wall,
said compartments having a space above said inner wall, for separating a gas phase from a liquid phase during thermal conversion,
said compartments being connected to an outlet valve (204a, 204b, . . . 204i),
allowing said hydrolysis mixture to flow through compartments of said vessel for a predetermined retention time, comprised between 3 and 16 minutes, to produce said mixture comprising 2-methacrylamide (MACRYDE),
opening all the outlet valve(s) of the vessel downstream from an outlet valve, which is determined depending on said predetermined retention time, and said predetermined feed rate.

2. The process of claim 1, wherein said thermal conversion vessel comprises at least three compartments (C1, C2, C3, ,.Ci) separated from each other by an overflow wall (205a, 205b, . . . , 205i), over which the hydrolysis mixture to be converted flows to pass from one compartment to the other, each compartment being connected to an outlet valve (204a, 204b, . . . 204i).

3. The process of claim 2, wherein in said thermal conversion vessel a height (h) of either overflow walls (205a, 205b, . . . , 205i) or inner wall (206a, 206b, . . . 206i) is between ⅔ and ¾ of the height (H) of the vessel.

4. The process of claim 1, wherein in said thermal conversion vessel the inner wall (206a, 206b, . . . 206i) is fixed to the side wall of the vessel.

5. The process of claim 1, wherein said thermal conversion vessel does not contain any agitator element.

6. The process of claim 1, wherein said thermal conversion vessel further comprises an opening (203) for feeding with said hydrolysis mixture, said opening (203) being at the top of the vessel and each said outlet valve (204a, 204b, . . . 204i) is at the bottom of said vessel.

7. The process of claim 2, wherein in said thermal conversion an overall number of overflow and inner walls is comprised between 3 and 32.

8. The process of claim 1, wherein said thermal conversion vessel has a cylindrical shape.

9. The process of claim 1, wherein said thermal conversion vessel comprises a manhole (201a, 201b) at, at least, one end.

10. The process of claim 2, wherein said thermal conversion vessel's side walls comprise flanges (220) regularly spaced on which are fixed the overflow walls and inner walls.

11. The process of claim 2, wherein said thermal conversion vessel and its overflow walls and inner walls are made of alloy chosen at least amongst: nickel based or tantalum alloys.

12. The process of claim 1, wherein said thermal conversion vessel further comprises a vent (209) and a bursting disk (208).

13. The process of claim 1, wherein said thermal conversion vessel further comprises at least two temperature sensors (207a, 207b, . . . , 207i) and at least one pressure sensor (211).

14. The process of claim 1, wherein said hydrolysis mixture further comprises an inhibitor of polymerization, which is soluble acid.

15. Process for amidification of ACH according to claim 1, wherein the feed rate is regulated according to a predetermined quantity of production, the outlet valves having to be opened for having a predetermined retention time are determined according to said feed rate, and heating temperature is regulated according to said retention time.

* * * * *